United States Patent
Imada et al.

(10) Patent No.: US 11,555,463 B2
(45) Date of Patent: Jan. 17, 2023

(54) GAS SENSOR ELEMENT AND GAS SENSOR

(71) Applicant: DENSO CORPORATION, Kariya (JP)

(72) Inventors: Shota Imada, Kariya (JP); Tomotaka Mouri, Kariya (JP); Toru Takeuchi, Kariya (JP)

(73) Assignee: DENSO CORPORATION, Kariya (JP)

( * ) Notice: Subject to any disclaimer, the term of this patent is extended or adjusted under 35 U.S.C. 154(b) by 314 days.

(21) Appl. No.: 16/786,135

(22) Filed: Feb. 10, 2020

(65) Prior Publication Data

US 2020/0182182 A1 Jun. 11, 2020

Related U.S. Application Data

(63) Continuation of application No. PCT/JP2018/030787, filed on Aug. 21, 2018.

(30) Foreign Application Priority Data

Aug. 22, 2017 (JP) .............................. JP2017-159693

(51) Int. Cl.
*G01N 33/00* (2006.01)
*G01N 27/407* (2006.01)
*F02D 41/14* (2006.01)

(52) U.S. Cl.
CPC ..... *F02D 41/1454* (2013.01); *F02D 41/1493* (2013.01); *G01N 33/006* (2013.01); *G01N 27/4072* (2013.01); *G01N 27/4077* (2013.01)

(58) Field of Classification Search
CPC .......................... G01N 33/006; G01N 27/4077
See application file for complete search history.

(56) References Cited

U.S. PATENT DOCUMENTS

| | | | |
|---|---|---|---|
| 2003/0159928 A1 * | 8/2003 | Kojima | G01N 27/4067 204/408 |
| 2009/0255812 A1 | 10/2009 | Yoshida et al. | |
| 2012/0297861 A1 | 11/2012 | Murai et al. | |

(Continued)

FOREIGN PATENT DOCUMENTS

| | | | | |
|---|---|---|---|---|
| DE | 102014113274 A1 * | 3/2015 | .......... | G01M 15/104 |
| DE | 102014222379 A1 * | 5/2016 | ......... | G01N 27/4077 |

(Continued)

OTHER PUBLICATIONS

DE-102014222379-A1—English (Year: 2016).*

*Primary Examiner* — Daniel S Larkin
*Assistant Examiner* — Fatemeh Esfandiari Nia
(74) *Attorney, Agent, or Firm* — Nixon & Vanderhye P.C.

(57) ABSTRACT

A gas sensor element comprising a long plate-like element body and a porous protective layer protecting a surface of the element body, wherein the element body has a gas detection part at an end thereof on one end face side in a longitudinal direction, and the protective layer includes an end face part covering the one end face in laminate, side face parts covering side faces connected to the one end face in laminate, and corner parts where two adjacent ones of the end face part and the side face parts meet. An outer surface of one or more of the end face part and the side face parts has a concave shape that is smoothly continuous with the corner parts and configured such that a layer thickness increases toward the corner parts.

12 Claims, 13 Drawing Sheets

(56) References Cited

U.S. PATENT DOCUMENTS

| | | | |
|---|---|---|---|
| 2015/0075254 A1* | 3/2015 | Sakuma | G01N 27/4072 |
| | | | 73/23.31 |
| 2015/0114085 A1* | 4/2015 | Iwano | B05D 1/36 |
| | | | 427/372.2 |
| 2015/0276661 A1 | 10/2015 | Moriyama et al. | |
| 2017/0343505 A1* | 11/2017 | Ito | G01N 33/0047 |

FOREIGN PATENT DOCUMENTS

| | | |
|---|---|---|
| JP | 2007-132954 | 5/2007 |
| JP | 2007-218894 | 8/2007 |
| JP | 2009-080110 | 4/2009 |

* cited by examiner

GAS SENSOR ELEMENT AND GAS SENSOR

CROSS-REFERENCE TO RELATED APPLICATION

The present application is a continuation application of International Application No. PCT/JP2018/030787 filed on Aug. 21, 2018, which claims priority to Japanese Application No. 2017-159693 filed on Aug. 22, 2017. The contents of these applications are incorporated herein by reference in their entirety.

BACKGROUND

Technical Field

The present disclosure relates to a gas sensor element and a gas sensor.

Background Art

The exhaust system of an automobile engine is provided with a gas sensor for detecting a specific exhaust gas, and emission control is performed by executing, for example, combustion control based on the detection result of the gas sensor.

SUMMARY

One aspect of the present disclosure is:

A gas sensor element comprising a long plate-like element body and a porous protective layer, wherein
the element body has a gas detection part, and
the protective layer includes an end face part, side face parts covering side faces, and corner parts, and, an outer surface of one or more of the end face part and the side face parts has a concave shape that is smoothly continuous with the corner parts and configured such that a layer thickness increases toward the corner parts.

Another aspect of the present disclosure is:

A gas sensor comprising the above-described gas sensor element to detect a specific gas component in a measured gas.

BRIEF DESCRIPTION OF THE DRAWINGS

The above and other objects, features, and advantages of the present disclosure will become clearer from the following detailed description with reference to the accompanying drawings. In the drawings.

DETAILED DESCRIPTION OF THE PREFERRED EMBODIMENTS

Figure 1:
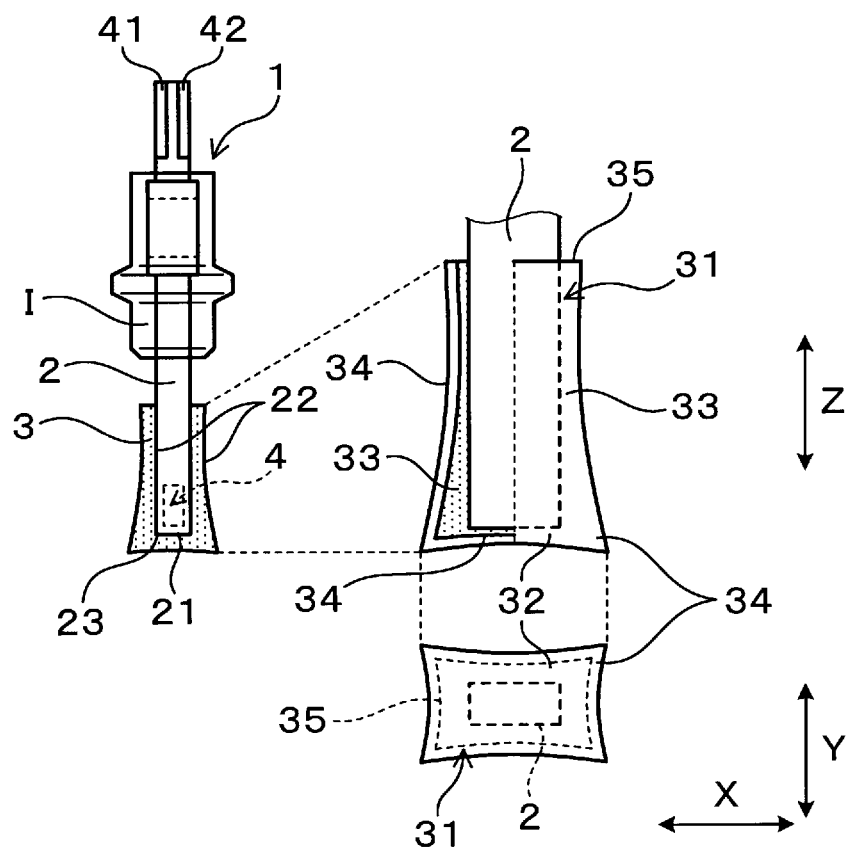
FIG. 1 shows an overall schematic view of a gas sensor element and an enlarged view of a main part thereof according to the first embodiment.

As disclosed in JP 2012-247293 A, a conventional gas sensor has a long plate-like gas sensor element accommodated in a cover body, and the gas sensor element is protected from intrusion of water droplets and poisoning substances by a porous protective layer provided on the outer surface. The gas sensor element is configured by incorporating a heater part in the element body in which a gas detection part is provided.

For example, the porous protective layer is usually formed by dipping the element body of the gas sensor element into a protective layer material in the form of slurry so that it has a certain coating thickness. In addition, according to this coating method, the thickness of the protective layer is reduced at the corners of the element body. Therefore, in JP 2012-247293 A, a first protective layer is formed in advance at the corners of the element body using, for example, the dispenser method. Then, a second protective layer that covers the entire outer periphery including the first protective layer is formed so that the thickness of the protective layer at the corners of the element body is larger than that of the edges of the element body.

In recent years, the regulations on exhaust gas of automobiles have been tightened, and it is required to activate the gas sensor at a rapid stage in order to further reduce emissions. However, to achieve this, the gas sensor needs to be activated at the time of starting the engine upon which water exposure is likely to occur. Further, the diameter of the through holes in the cover body tends to increase in order to increase the amount of gas inflow. In such case, since the gas sensor element is repeatedly exposed to water and the diameter of the water droplets reaching the gas sensor element increases, the water exposure stress increases and the water exposure resistance deteriorates.

Further, it has been found that, at such timing, if a part of a heated element body is repeatedly exposed to water, the surface of the protective layer tends to peel off. Thus, even if there is no problem immediately after a single water exposure, peeling may gradually progress as the number of times of water exposure increases. In particular, it has been found that when peeling progresses in the vicinity of the corners of the element body and the thickness of the protective layer cannot be secured, element cracking may occur.

An object of the present disclosure is to provide a gas sensor element and a gas sensor capable of reducing peeling of the porous protective layer covering the surface of the element body even in an environment in which repeated water exposure occurs, and capable of achieving both rapid activation and water exposure resistance.

One aspect of the present disclosure is:

A gas sensor element comprising a long plate-like element body and a porous protective layer protecting a surface of the element body, wherein the element body has a gas detection part at an end thereof on one end face side in a longitudinal direction, and the protective layer includes an end face part covering the one end face in laminate, side face parts covering side faces connected to the one end face in laminate, and corner parts where two adjacent ones of the end face part and the side face parts meet, and, an outer surface of one or more of the end face part and the side face parts has a concave shape that is smoothly continuous with the corner parts and configured such that a layer thickness increases toward the corner parts.

Another aspect of the present disclosure is:

A gas sensor comprising the above-described gas sensor element to detect a specific gas component in a measured gas, comprising a cylindrical housing supporting an outer periphery of the gas sensor element, and a cover body attached to one end of the cylindrical housing, wherein an end of the gas sensor element at which the protective layer is provided is housed in the cover body, and the measured gas is introduced into the cover body through a through hole provided in the cover body.

For rapid activation of the gas sensor element, it is advantageous that the heat capacity of the protective layer covering the element body is small. The outer surface of the protective layer is configured to have a concave shape so as to partially reduce the layer thickness of the protective layer, whereby its mass and heat capacity can be reduced. In addition, since the concave shape of the outer surface of the protective layer makes the layer thickness at the corner parts relatively large, it is possible to reduce the heat capacity while securing the layer thickness at the element corners which are relatively weak against moisture exposure.

When the protective layer is exposed to water, the water droplets that adhere to the surface of the protective layer soak into the interior, and at the same time, they evaporate taking away the heat capacity of the protective layer. If there is a portion in the surface of the protective layer where such soaking and evaporation tend to occur, repeated water exposure may cause local peeling. However, the water droplets spread easily on the surface of the protective layer having a concave shape. In addition, by forming the surface shape smoothly continuous with the corner parts, it is possible to prevent thermal stress concentrating on a portion to cause peeling or the like.

Thus, since the end face part or the side face parts of the protective layer covering the element body are configured to have a concave shape that is smoothly continuous with the corner parts, the heat capacity can be reduced to enable rapid activation, while still protecting the element corners.

A gas sensor employing such a gas sensor element can be relieved of the restrictions on the arrangement and size of the through holes of the cover body for protection of the gas sensor element. For example, the diameter of the through holes of the cover body can be increased to increase the amount of gas introduced. Thus, the specific gas component in the measured gas can be detected with good responsiveness.

Therefore, according to the above-described aspects, it is possible to provide a gas sensor element and a gas sensor capable of reducing peeling of the porous protective layer covering the surface of the element even in an environment in which repeated water exposure occurs, and capable of achieving both rapid activation and water exposure resistance.

First Embodiment

Embodiments according to a gas sensor element and a gas sensor will be described with reference to FIGS. 1 to 15. The gas sensor element 1 shown in FIGS. 1 and 2 constitutes the main part of the gas sensor S shown in FIG. 3, and is inserted into a cylindrical insulator I such that its outer periphery is supported by the cylindrical housing H. The gas sensor S may be applied to, for example, an exhaust gas purification system for an automobile engine in order to detect the concentration of a specific gas in the exhaust gas which is the gas to be measured. Specifically, it can be used for an oxygen sensor for detecting oxygen concentration, an air-fuel ratio sensor for detecting the air-fuel ratio (i.e., A/F) based on oxygen concentration, and the like.

In FIG. 1, the gas sensor element 1 includes a long plate-like element body 2 held inside the insulator I, and a porous protective layer 3 protecting the surface of the element body 2. The longitudinal direction Z of the element body 2 is the vertical direction in the drawing, and the element body 2 has a gas detection part 4 at an end thereof on the side of a tip end face 21 which is one of the end faces thereof in the longitudinal direction Z (that is, the lower end face side in FIG. 1). For example, the element body 2 can have a rectangular parallelepiped shape, and the directions of the two sides of its rectangular cross section (that is, the directions orthogonal to the longitudinal direction Z) are hereinafter referred to as a long side direction X and a short side direction Y.

The protective layer 3 is provided so as to cover the outer periphery of the end of the element body 2 on the side of the tip end face 21 protruding from the insulator I. The protective layer 3 includes an end face part 32 that covers the tip end face 21 of the element body 2 in laminate, a plurality of side face parts 33 that cover the side faces 22 that are continuous with the tip end face 21 in laminate, and corner parts 34 which are each connected to two adjacent ones of the end face part 32 and the side face parts 33. One or more of the end face part 32 and the side face parts 33 have such a concave shape that the outer surface 31 is smoothly continuous with the corner parts 34, and the layer thickness increases as it approaches the corner parts 34.

The gas sensor S is used in an environment exposed to the exhaust gas which is the gas to be measured. The protective layer 3 in the gas sensor element 1 that covers the element body 2 protects the element body 2 from condensed water and poisoning substances contained in the exhaust gas. When the outer surface 31 of the end face part 32 and the side face parts 33 of the protective layer 3 are formed in desired concave shapes and formed in such a manner that the corner parts 34 have the maximum thickness, both rapid activation and water exposure resistance can be achieved.

The detailed configurations of the protective layer 3 and outer surface 31 formed in the gas sensor element 1 will be described later.

Figure 3:
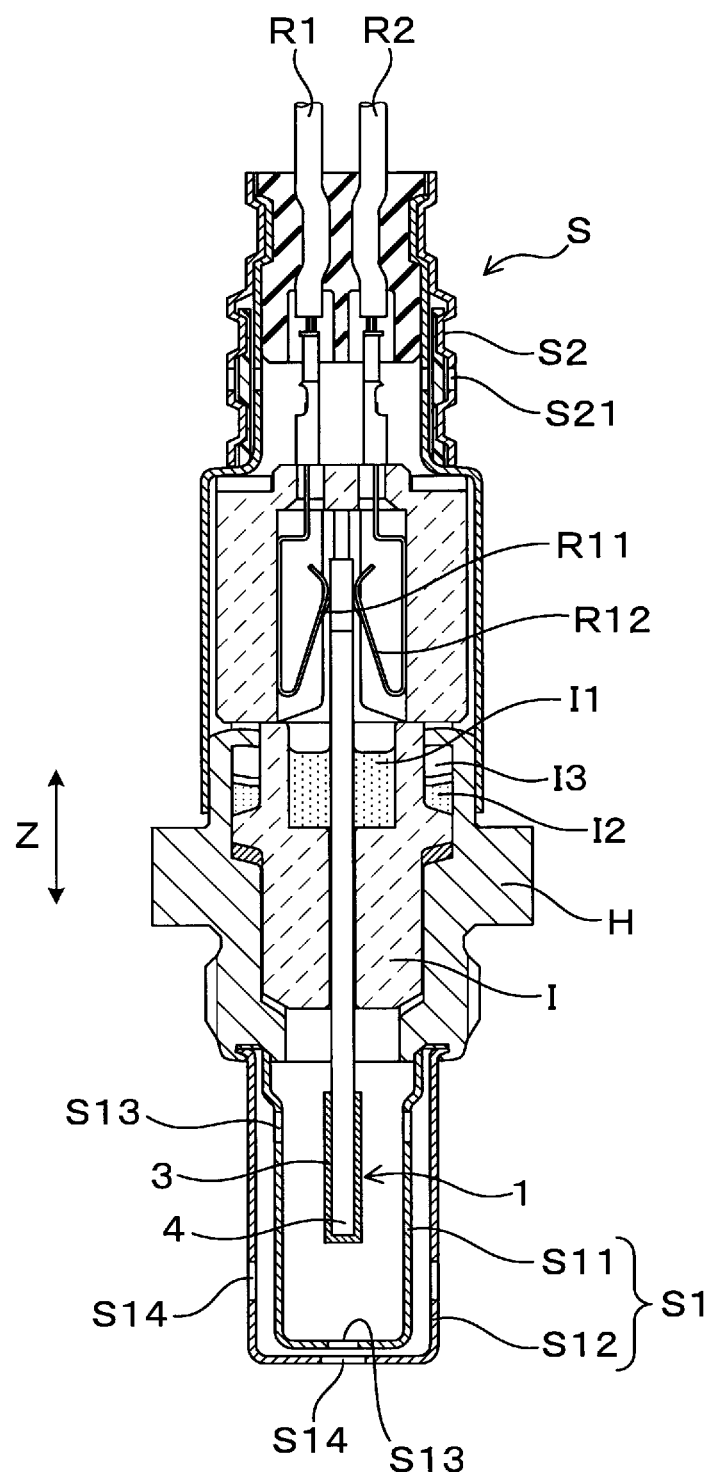
FIG. 3 is an overall cross-sectional view of a gas sensor comprising the gas sensor element according to the first embodiment.

In FIG. 3, the gas sensor S has a cylindrical housing H whose axial direction is the longitudinal direction Z of the gas sensor element 1 (that is, the vertical direction in the figure), and the gas sensor element 1 is inserted and held in the housing H. In the gas sensor S and the gas sensor element 1, one end side thereof having the gas detection part 4 is referred to as the tip end side (that is, the lower end side in the drawing), and the opposite side is referred to as the base end side (that is, the upper end side in the drawing). An element cover S1 as a cover body is attached to the tip end side of the housing H, and the tip end of the gas sensor element 1 protrudes from the housing H and is accommodated in the element cover S1. Similarly, an atmosphere side cover S2 is attached to the base end side of the housing H (that is, the upper end side in the drawing), and the base end of the gas sensor element 1 protrudes from the housing H and is accommodated in the atmosphere side cover S2.

The element cover S1 is in the form of inner and outer-doubled and bottomed cylinders, and is arranged so as to surround the periphery of the tip end of the gas sensor element 1. The inner cover S11 and the outer cover S12 of the element cover S1 are provided with through holes S13 and S14 serving as exhaust gas entry/exit holes on the side faces and the bottom face, respectively. When the exhaust gas that has passed through the through holes S13 and S14 reaches the surface of the gas sensor element 1, it is taken into the interior via the protective layer 3. The cylindrical atmosphere-side cover S2 is provided with a through hole S21 that opens at the outer peripheral side face to serve as an atmosphere hole, and it takes in the atmospheric air inside.

The outer periphery of the intermediate part of the gas sensor element 1 is held inside the cylindrical insulator I accommodated in the housing H, and sealing glass I1 is filled between the opening of the insulator I on the base end side and the gas sensor element 1. The intermediate large-diameter part of the insulator I is supported on a stepped part of the housing H, and talc powder 12 is filled between the outer peripheral surface of the insulator I and the inner peripheral surface of the housing H. Then, the thinned part of the base end of the housing H is crimped interposing a cylindrical insulating member 13 in order to fix the insulator.

Figure 2:
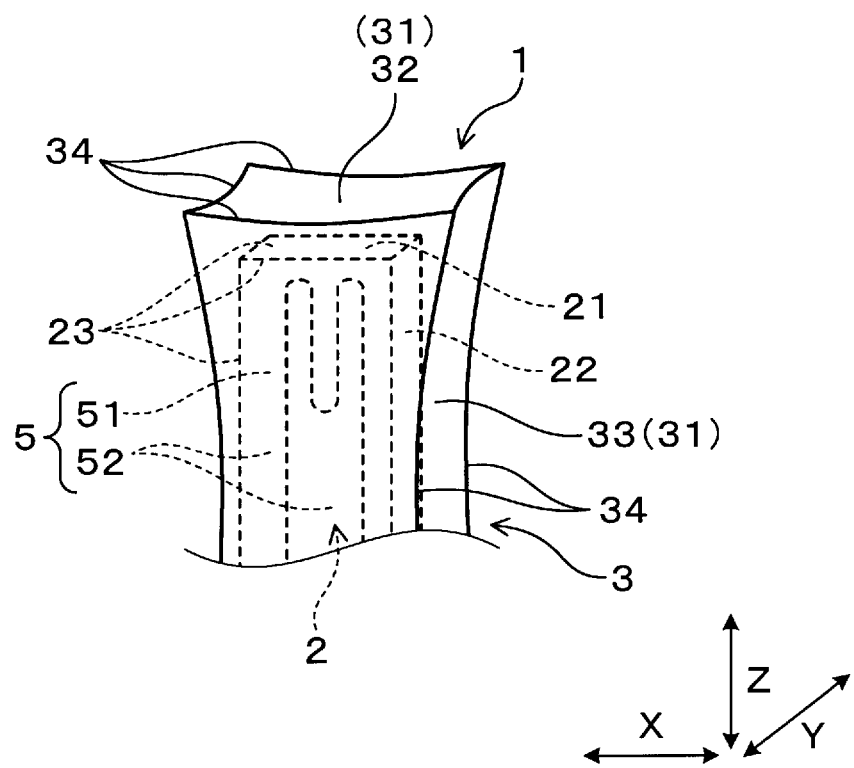
FIG. 2 is an enlarged perspective view showing the configuration of the main part of the gas sensor element according to the first embodiment.

A plurality of lead wires R1 and R2 connected to an external engine control unit (not shown) are insulated and held at the base end opening of the atmosphere-side cover S2. Terminal parts R11 and R12 are provided on the tip end side of the lead wires R1 and R2, and they are electrically connected to electrode terminal parts 41 and 42 (see, for example, FIG. 1) provided at the base end of the gas sensor element 1. Further, as shown in FIG. 2, the gas sensor element 1 includes a heater part 5 incorporated in the element body 2 on the tip end face 21 side. The heater part 5 includes a heater electrode 51 and a lead part 52 for energization. The heater electrode 51 is caused to generate heat by external energization from the outside, so that the portion corresponding to the gas detection part 4 of the element body 2 is activated at an activation temperature.

Figure 4:
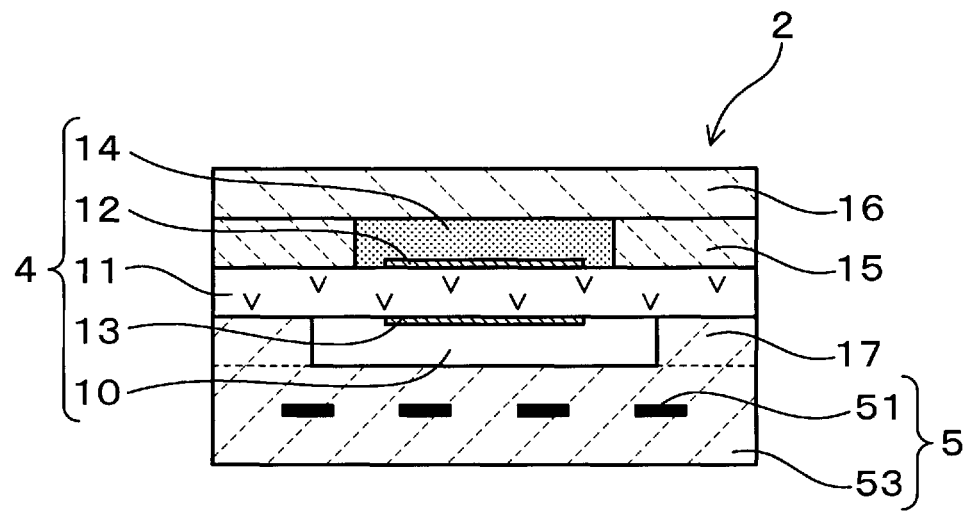
FIG. 4 is a cross-sectional view showing the structure of the gas detection part of the gas sensor element according to the first embodiment.

As shown in FIG. 4, the gas detection part 4 of the gas sensor element 1 comprises, for example, an oxide-ion-conductive solid electrolyte body 11, a measured-gas-side electrode 12 provided on the surface of the solid electrolyte body 11 on the measured gas side and into which the gas to be measured is introduced via a porous diffusion resistance layer 14, and a reference-gas-side electrode 13 provided on the surface of the solid electrolyte body 11 on the reference gas side so as to face a reference gas chamber 10. The porous diffusion resistance layer 14 is formed by making a part of the diffusion resistance layer forming layer 15, laminated over the solid electrolyte body 11, with a porous body, and this communicates with a gas inlet (not shown). A dense shielding layer 16 is laminated over the face of the porous diffusion resistance layer 14 opposite to the solid electrolyte body 11.

A reference gas chamber forming layer 17 forming the reference gas chamber 10 has a heater substrate 53 laminated on the face opposite to the solid electrolyte body 11, and the heater electrode 51 is embedded in the heater substrate 53 to constitute the heater part 5. The element body 2 is formed by sequentially laminating the heater substrate 53, the reference gas chamber forming layer 17, the solid electrolyte body 11, the porous diffusion resistance layer 14, the diffusion resistance layer forming layer 15, and the shielding layer 16.

Although the element body 2 has a rectangular cross-sectional shape in this example, it may have a polygonal cross-sectional shape. For example, instead of making the two ends on the gas detection part 4 side and the heater part 5 side right-angled corners as shown in the figure, they may be chamfered so as to have a cross-sectional shape of a hexagon or an octagon. In such a case as well, the protective layer 3 is provided so as to conform to the shape of the element body 2, and the side face parts 33 and the corner parts 34 in the form of a layer covering the side faces 22 of the polygon are formed in laminate.

The solid electrolyte body 11 is made of, for example, a zirconia-based solid electrolyte, and the heater substrate 53, the reference gas chamber forming layer 17, the porous diffusion resistance layer 14, the diffusion resistance layer forming layer 15, and the shielding layer 16 are made of, for example, an insulating ceramic such as alumina.

Thereby, when the exhaust gas is introduced to the measured-gas-side electrode 12 via the porous diffusion resistance layer 14, and a certain voltage is applied between the measured-gas-side electrode 12 and the reference-gas-side electrode 13 on the side of the reference gas chamber 10 into which the atmospheric air is introduced, the sensor output of the gas detection part gives a sensor output exhibiting limiting current characteristics corresponding to the oxygen concentration. By utilizing this, an air-fuel ratio signal corresponding to the oxygen concentration in the exhaust gas can be obtained.

Next, the detailed structure of the protective layer 3 will be described.

As shown in FIG. 1 in an enlarged manner, the protective layer 3 covers, in laminate, the outer periphery of the end of the element body 2 on the tip end face 21 side, that is, covers the entire tip end face 21 as well as the end parts of the side faces 22 connected thereto. The outer shape of the protective layer 3 conforms to the outer shape of the element body 2, and the protective layer 3 is larger than the element body 2 by the thickness of itself. Here, the proximal half has a shape generally similar to that of the element body 2, and the tip half has a tapered shape whose layer thickness increases toward the tip end face 21 side.

As shown in FIG. 2, the protective layer 3 has an end face part 32 that covers the tip end face 21 in laminate, and four side face parts 33 that cover the four side faces 22 connected to the tip end face 21 in laminate. The corner parts 34 are formed between the end face part 32 and each of the side face parts 32, or between two adjacent side face parts 32. The corner parts 34 are located outside elements corners 23 formed between the tip end face 21 and the side faces 22 of the element body 2 or between two adjacent side faces 22.

The end face part 32 of the protective layer 3 is formed outside the tip end face 21 of the element body 2 so as to have a generally rectangular outer shape (see, for example, FIG. 1) that is larger than that of the tip end face 21 and whose four corners protrude outward. The outer surface 31 of the end face part 32 is formed in a concave shape that is smoothly continuous with the corner parts 34 formed between it and the four side face parts 33, and the layer thickness increases toward the corner parts 34 at the two ends in each of the long side direction X and the short side direction Y of the rectangle. As shown in FIG. 1, the outer shape of the end 35 of the protective layer 3 on the base end side is substantially similar to the outer shape of the end face part 32 but the former is smaller.

Similarly, the side face parts 33 of the protective layer 3 are provided outside the side faces 22 connected to the tip end face 21 of the element body 2, and they have a substantially trapezoidal outer shape that is larger than that of the side faces 22 and tapered so as to broaden toward the tip end side (that is, the upper end side in FIG. 2). The outer surface 31 of each of the side face parts 33 is also formed in a concave shape that is smoothly continuous with the corner parts 34 formed between two adjacent side face parts 33 or between the side face part and the end face part 32, and the layer thickness increases toward the corner part 34 on the tip end side in the longitudinal direction Z, and the layer thickness increases toward the corner parts 34 at the two ends in the long side direction X or the short side direction Y.

Preferably, the outer surface 31 of each of the end face part 32 and the side face parts 33 of the protective layer 3 covering each face of the element body 2 is formed into a concave shape that is smoothly continuous with the corner parts 34. Specifically, for example, the entire face may be a smooth curved surface, or at least a part of it may be a smooth curved face connected to the corner parts 34. In this case, the concave shape having a smooth curved surface suffices if it has such a shape that, in a cross section in the longitudinal direction Z or a direction perpendicular thereto, the outer surface 31 of the protective layer 3 has a contour line 311 including a smoothly continuous curved part.

Figure 5:
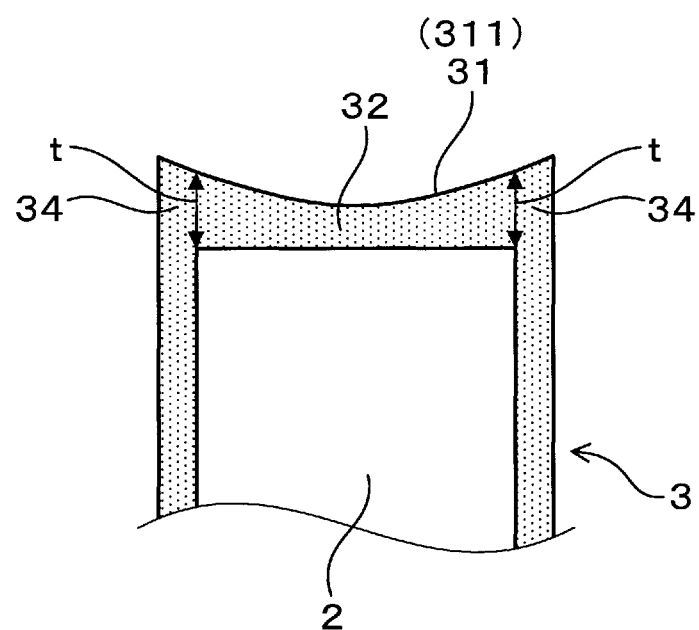
FIG. 5 is an enlarged cross-sectional view of the main part for showing an example of the shape of the end face part of the protective layer of the gas sensor element according to the first embodiment.
Figure 6:
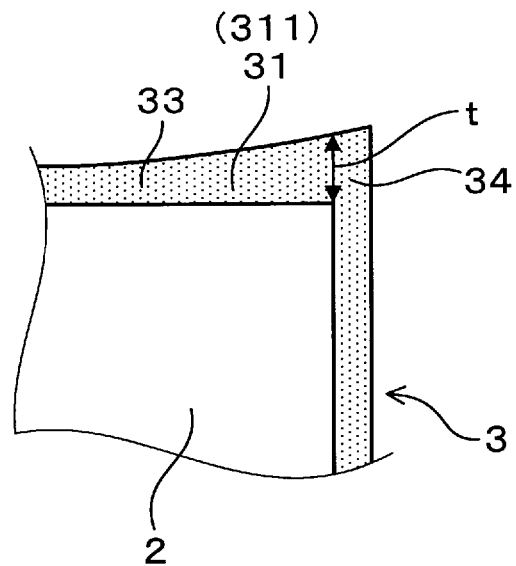
FIG. 6 is an enlarged cross-sectional view of the main part for showing an example of the shape of the side face part of the protective layer of the gas sensor element according to the first embodiment.

For example, in the longitudinal cross section of the end face part 32 of the protective layer 3 shown in FIG. 5, the contour line 311 of the outer surface 31 is a smooth continuous curved line extending between the corner parts 34 at the two ends, and the layer thickness t is thicker at the two corner parts 34. Similarly, in the longitudinal cross section of the side face parts 33 of the protective layer 3 shown in FIG. 6, the contour line 311 of the outer surface 31 is a smooth continuous curved line extending from the corner part 34 on the tip end side toward the base end side, and the layer thickness t is thicker at the corner part 34 on the tip end side. The cross section of the side face parts 33 in the direction orthogonal to the longitudinal direction Z (that is, the long side direction X or the short side direction Y) is similar to the cross section of the end face part 32 shown in FIG. 5. These contour lines 311 may be partly linear, but it is desirable that they do not have an extreme change in shape such as a round-shaped abrupt inflection point or inflection point.

Note that the outer surface 31 of the end face part 32 and the side face parts 33 of the protective layer 3 are not limited to the shapes shown in FIGS. 1 and 2, and they may have any suitable concave shape that is smoothly continuous with the corner parts 34. For example, in FIGS. 1 and 2, the thickness of the side face part 33 of the protective layer 3 increases toward the tip end side, and the proximal half thereof has a substantially constant outer shape whose layer thickness does not change in the cross section in the longitudinal direction Z. However, as shown in the left diagram of FIG. 7, the side face part 33 of the protective layer 3 may have such a shape that the layer thickness also increases toward the end 35 on the base end side in the longitudinal direction Z. In this case, the layer thickness is largest at the two ends in the longitudinal direction Z, that is, the end part 35 on the base end side and the corner part 34 at the outer periphery of the end face part 32 on the tip end side, and the thickness gradually decreases toward the middle part in the longitudinal direction Z. In the long side direction X or the short side direction Y, the layer thickness increases as it approaches the corner parts 34 at the two ends. That is, they have a concave shape that is entirely formed of a smooth curved face.

Figure 7:
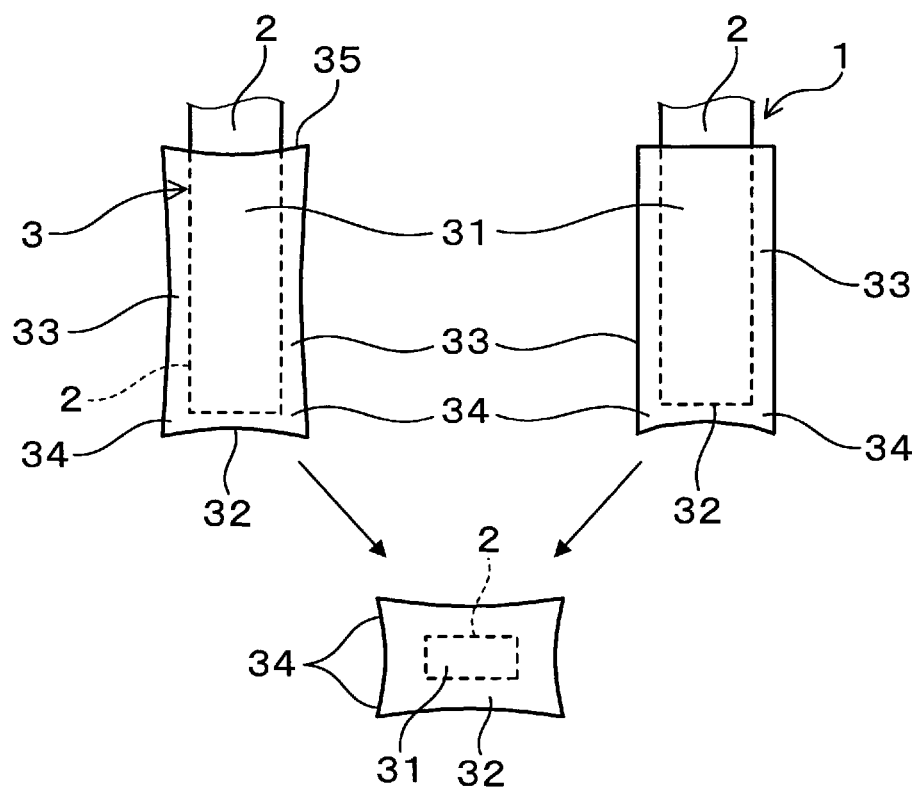
FIG. 7 is an enlarged view of the main part for showing another example of the configuration of the main part of the gas sensor element according to the first embodiment.

Alternatively, as shown in the right diagram of FIG. 7, the side face parts 33 of the protective layer 3 may have such a shape that the layer thickness in the cross section in the longitudinal direction Z is substantially constant. In the cross section in the long side direction X or the short side direction Y, the side face parts 33 have a layer thickness that increases toward the corner parts 34 at the two ends as with the above case, and they have a smooth concave shape as a whole. Here, the shape of the end face part 32 corresponding to the side face parts 33 of the left diagram and the right diagram of FIG. 8 is a smooth concave shape similar to that of the end face part 32 shown in FIGS. 1 and 2 in both of the cases.

When the end face part 32 and the side face parts 33 of the protective layer 3 are formed into concave shapes as described above, the layer thickness is largest at the corner parts 34 located on the outer peripheral edges of each face part, and thus it is possible to protect the element corners 23 which are the weakest parts against water exposure. In addition, since the layer thickness can be reduced at parts other than the corner parts 34, the mass of the protective layer 3 is reduced, which leads to a reduced heat capacity, and earlier activation becomes possible. Further, when water exposure occurs, since the water droplets spread on the smooth concave outer surface 31, an effect of suppressing the progress of peeling can be obtained. The peeling phenomenon and the effect of the shape of the protective layer 3 will be described next.

When the gas sensor S is activated, the gas detection part 4 is heated to the activation temperature by energizing the heater part 5 of the gas sensor element 1 shown in FIG. 2. In FIG. 8, when the protective layer 3 is in a high temperature stable state, the surface temperature is, for example, between 400° C. and 600° C., and when condensed water (for example, about 60° C.) intrudes into the cover body S1 of the gas sensor S, a part of it adheres to the outer surface 31 of the protective layer 3 as a water droplet W (see, for example, FIG. 8(1)). The water droplet W spreads on the protective layer 3, and soaks into the outer surface 31 and evaporates at the same time (see, for example, FIG. 8(2)).

Figure 8:
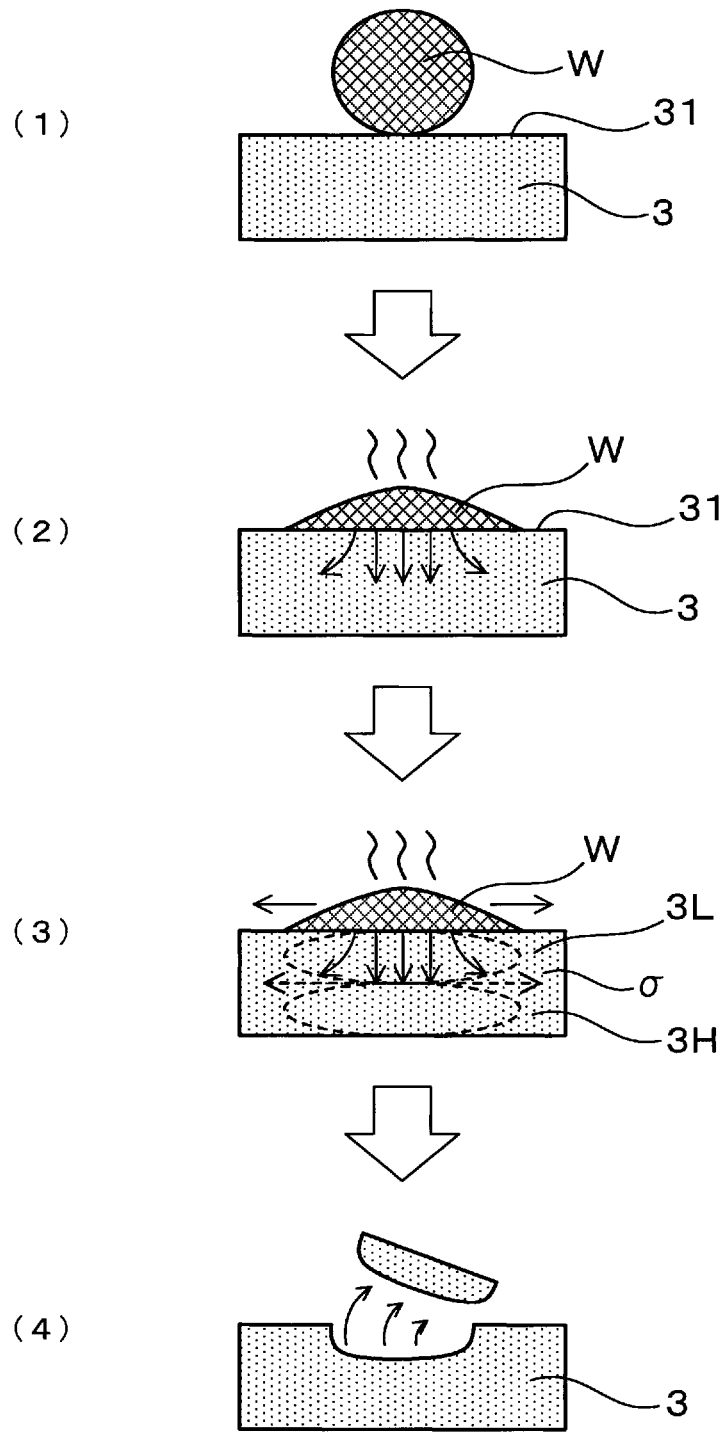
FIG. 8 is a schematic view for explaining the mechanism of the surface peeling caused by water exposure of the gas sensor element according to the first embodiment.
Figure 9:
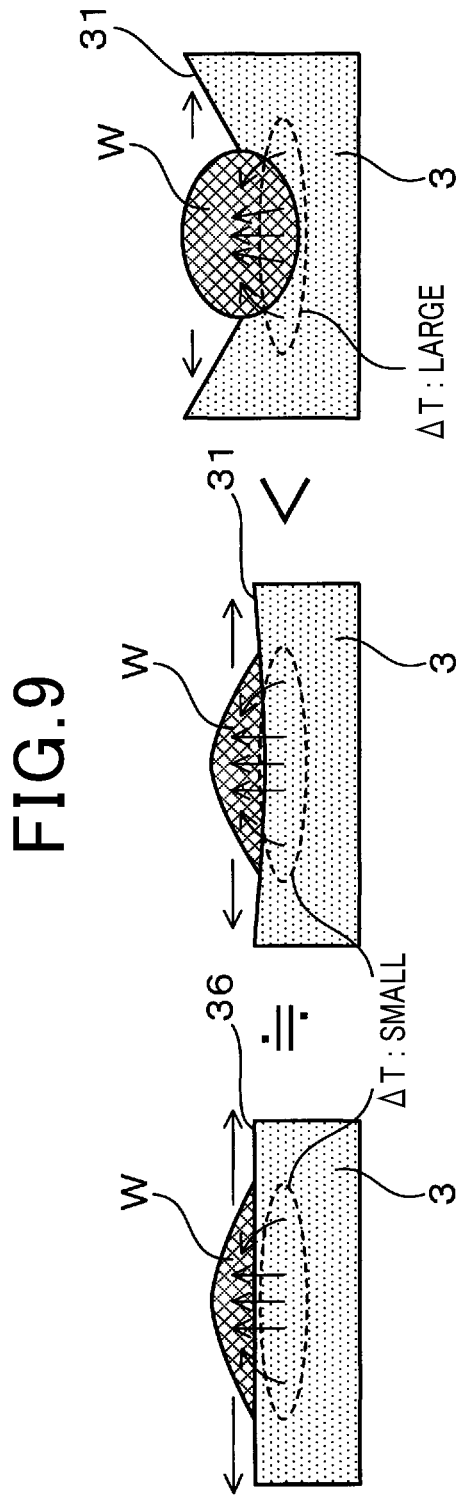
FIG. 9 is a schematic view for explaining the relationship between the surface shape of the protective layer of the gas sensor element according to the first embodiment and the thermal stress.

When soaking of the water droplet W occurs, a difference in thermal expansion occurs in the protective layer 3, and therefore a stress due to the thermal expansion difference is generated in the vicinity of the location in the protective layer 3 to which the permeated water has reached (see, for example, FIG. 8(3)). This thermal stress a is expressed by the following Eq. 1. In Eq. 1, a is the linear expansion coefficient, E is the Young's modulus, and $\Delta T$ is the temperature change.

$$\sigma = a \times E \times \Delta T \qquad \text{Eq. 1:}$$

That is, a thermal stress is generated between the low temperature part 3L into which the water droplet W has permeated and the high temperature part 3H in contact with the lower part of the low temperature part, and the low temperature part 3L undergoes thermal contraction. If this thermal contraction due to water exposure occurs repeatedly at the same location, fatigue failure occurs inside the protective layer 3 which results in peeling (for example, see FIG. 8(4)).

More specifically, the protective layer 3 is a porous body, and a large number of pores exist between the ceramic material particles 3P. Due to these pores, the infiltration paths of the water droplet W formed inside the protective layer 3 include gaps between distorted particle surfaces and particles, and when the spread of the water droplet W is suppressed at such parts, the stress tends to increase. It is considered that when repeated water exposure occurs at such stress-concentration parts, cracking in a particle or between particles progresses, and results in peeling due to fatigue failure.

Therefore, in order to prevent peeling due to repeated water exposure, it is preferable that the shape is capable of reducing the thermal stress due to infiltration of the water droplets W into the protective layer 3. Specifically, as shown in the middle diagram of FIG. 9, when the outer surface 31 of the protective layer 3 is a smooth curved concave surface, the water droplet W spreads substantially as easily as in the case of the flat surface 36 shown in the left diagram of FIG. 9, and the contact area with the water droplet W increases. On the other hand, as shown in the right diagram of FIG. 9, for example, even when the outer surface 31 is curved, if the curvature radius is small, the water droplet W does not spread and the contact area becomes small. When infiltration and evaporation of the water droplet W proceed at the same time as described above, if the amount of water exposure is the same, the heat capacity taken away will be the same regardless of the size of the contact area. Therefore, in the case of an outer surface 31 having a small curvature radius and a small contact area, since evaporation occurs locally, $\Delta T$ in Eq. 1 tends to increase and the thermal stress a tends to increase.

Thus, in order to reduce the thermal stress upon water exposure, the outer surface 31 of the protective layer 3 is preferably a smooth and gentle concave surface, and desirably does not have a surface shape having a portion with a small curvature radius. Preferably, the end face part 32 or the side face parts 33 of the protective layer 3 have a shape whose curvature radius at the minimum rounded portion of the contour line 311 forming the outer surface 31 in the cross section in the longitudinal direction Z, or the long side direction X or the short side direction Y orthogonal thereto is equal to or greater than 0.4 mm.

Next, a method of manufacturing the gas sensor element 1 will be described.

Figure 10:
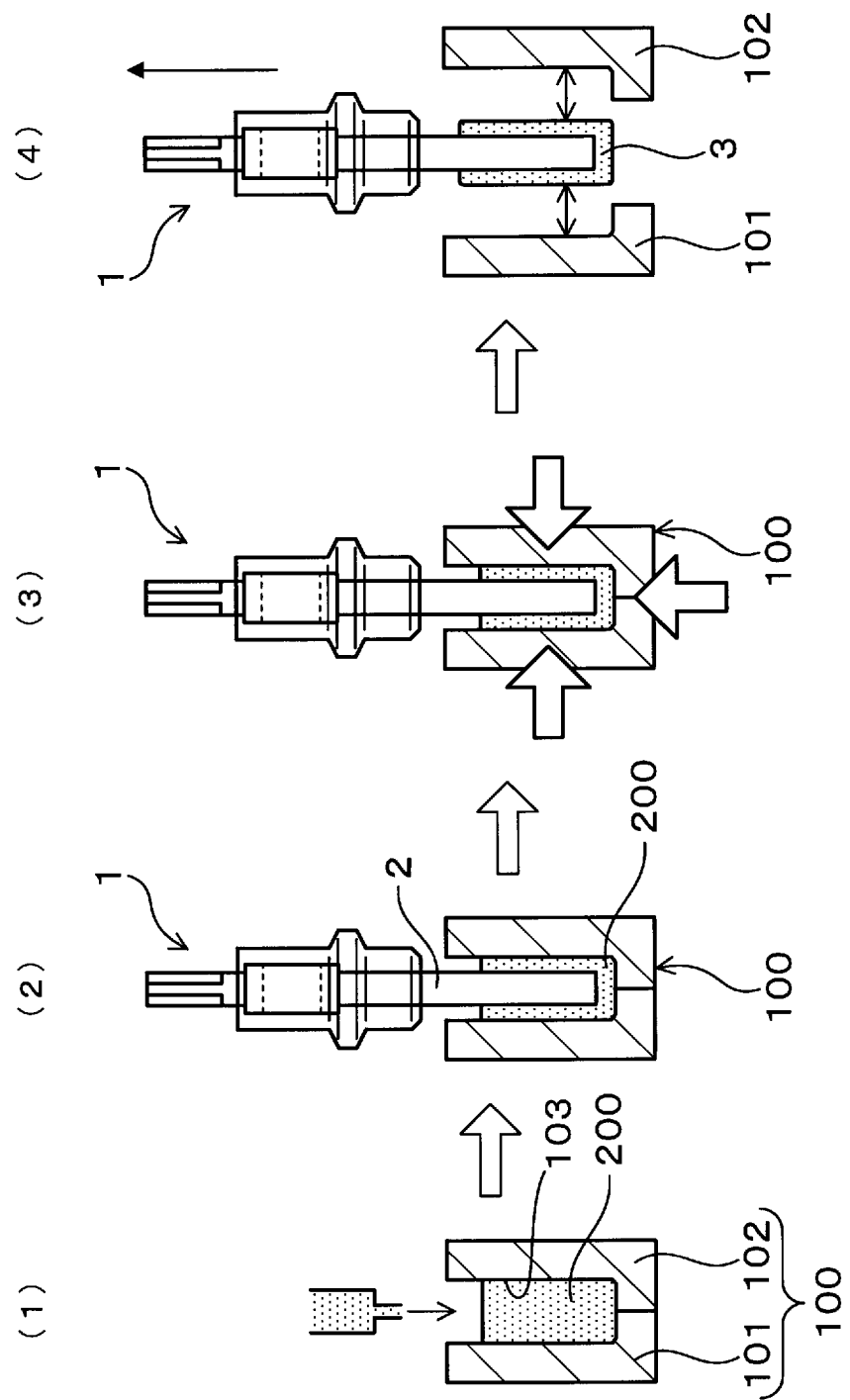
FIG. 10 is a view showing the manufacturing process of the gas sensor element according to the first embodiment.

As shown in FIG. 10, molding method can be adopted as the method of providing the protective layer 3 on the surface of the element body 2. In the step shown in (1), first, a slurry 200 containing a ceramic material constituting the protective layer 3 is injected into a mold 100 in the form of a container. The mold 100 may include, for example, two molds 101 and 102 having a split structure, and the hollow part 103 formed at the abutting parts of the two molds 101 and 102 may have a shape corresponding to the outer shape of the protective layer 3. For example, the protective layer 3 shown in FIG. 1 can be formed by forming the inner surface of each of the tip halves of the two molds 101 and 102 in a tapered shape that expands outward toward the tip end side.

The slurry 200 is a protective-layer-forming material prepared by adding an inorganic binder, a coagulant, and/or the like to the ceramic material for constituting the protective layer 3. In the step shown in (2), the element body 2 of the gas sensor element 1 is inserted from the upper opening of the hollow part into the mold 100 into which the slurry 200 has been injected, after positioning and holding it using a jig or the like (not shown), the slurry 200 is temporarily cured. After that, in the step shown in (3), the two molds 101 and 102 are opened to take out the gas sensor element 1 whose element body 2 is covered with the pre-cured slurry 200, and the gas sensor element is baked to form the protective layer 3.

Other than heat drying method, the curing method may be performed by adding a curing agent such as a UV resin or a thermosetting resin to the slurry 200 and performing UV irradiation or heat curing. As described above, when molding is employed, since the mold 100 can be formed into a shape corresponding to the protective layer 3 in advance, the protective layer 3 having an outer surface 31 with a desired concave shape can be formed with high accuracy. Alternatively, it is also possible to employ the mold 100 to form the protective layer 3, and after that, form the outer surface 31 of the protective layer into a concave shape by cutting or the like, or into any desired shape.

Experimental Example 1

Figure 11:
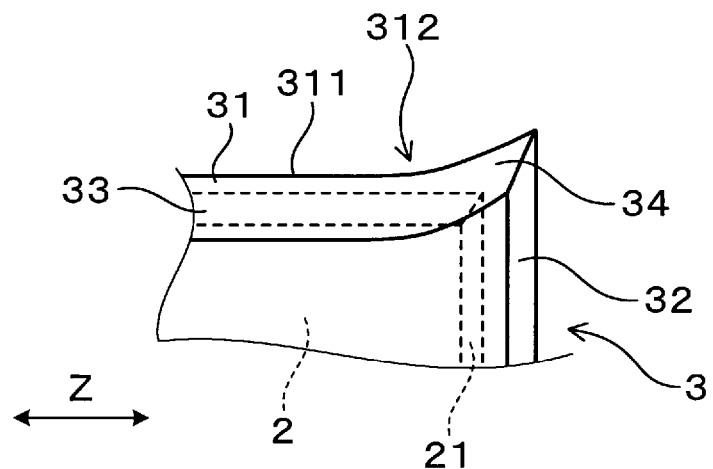
FIG. 11 is an enlarged perspective view of the main part showing the shape of the protective layers of the gas sensor element samples used in the water exposure test performed in Experimental Example 1.

Samples of the gas sensor element 1 prepared by the above-described method were tested to evaluate the water exposure resistance performance of the concave shape of the protective layer 3. As shown in FIG. 11, one of the side face parts 33 of the protective layer 3 of each sample of the gas sensor element 1 has a curved concave face, and the contour line 311 of the outer surface 31 in the cross section in the longitudinal direction Z is a continuous curved line. The layer thickness of the protective layer 3 increases as it approaches the corner part 34 on the tip end side. In the vicinity of the tip end face 21 of the element body 2, the contour line 311 has a minimum rounded portion 312 having the smallest curvature radius. Here, the layer thickness of the side face part 33 is substantially constant except for the vicinity of the corner part 34. Samples 1 to 8 with minimum rounded portions 312 that have different Curvature radius were prepared by varying the curve shape of the contour lines 311, and the following repeated water exposure test was performed on them.

Figure 12:
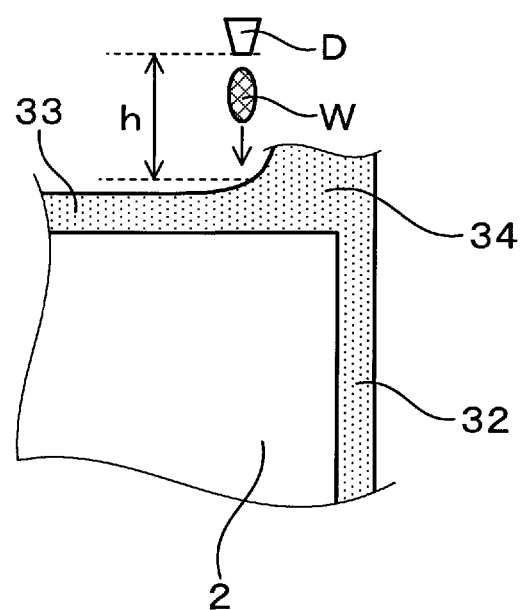
FIG. 12 is an enlarged cross-sectional view of the main part of the gas sensor element for explaining the method of the water exposure test performed in Experimental Example 1.

As shown in FIG. 12, in the repeated water exposure test, the heater part 5 was energized so that the gas sensor element 1 reaches a predetermined control temperature, and a predetermined amount of water droplet W whose temperature was controlled to about 50° C. to 70° C. was repeatedly dropped from a dispenser D onto the minimum rounded portion 312 of the protective layer 3. The dispenser D was placed at a predetermined height h from the dropping position, and when there were more than one minimum rounded portions 312, the water droplet was dropped on the position closest to the heat generation center of the heater. The dropping interval was set to a time that allows the surface of the protective layer 3 to recover to the stable temperature after dropping the water droplet W, and the surface state of the protective layer 3 was observed through images or a video while dropping the water droplets, and the number of times of water exposure it took to cause the protective layer 3 to peel off was counted. The control temperature of the gas sensor element 1 and the layer thickness of each section of the protective layer 3 were as follows, and the surface temperature of the protective layer 3 was measured with an infrared thermometer.

Figure 13:
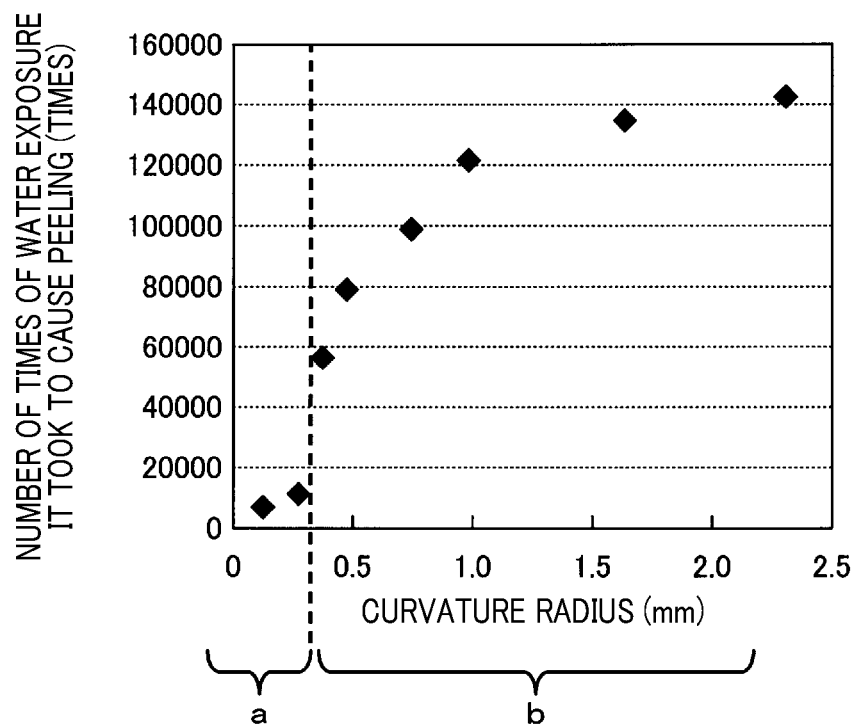
FIG. 13 is a graph showing the relationship between the curvature radius of the outer surface of the protective layer and the number of times of water exposures in Experimental Example 1.
Figure 14:
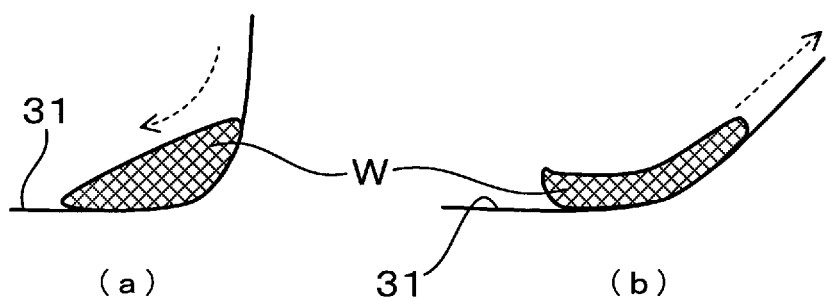
FIG. 14 is a schematic view for explaining the relationship between the curvature radius of the outer surface of the protective layer and the ease of a water droplet to spread in Experimental Example 1.

Controlled temperature: 750° C.
Water exposure amount: 2 μL
Layer thickness at corner part 34: about 250 μm
Layer thickness of side face part 33 except for vicinity of corner part 34: about 200 μm
Height h of dispenser D: 30 mm As shown in Table 1, the results of the repeated water exposure test show that even when 2 μL water droplets W are repeatedly dropped on the same location, if the outer surface 31 of the protective layer 3 has a curved concave shape and the layer thickness at the corner part 34 is increased, it is possible to withstand thousands of times of repeated water exposure. Further, as shown in FIG. 13 which shows the relationship between the curvature radius of the minimum rounded portion 312 and the number of times of water exposure, in the range b in which the curvature radius is equal to or larger than 0.4 mm, the number of times of water exposure it took to cause peeling rapidly increases, and the number of times of water exposure increases as the curvature radius increases until it converges in the vicinity of 2 mm. It can be considered that this is because, as shown in the left figure (a) of FIG. 14, in the range a in which the curvature radius is smaller than 0.4 mm, gravity and surface tension acting on the water droplet W suppress the spreading of the water droplet W, and the shape of the water droplet W does not change greatly. On the other hand, as shown in the right figure (b) of FIG. 14, in the range b in which the curvature radius is larger, the force of the water droplet W to spread outward is superior to gravity and surface tension. As a result, the shape of the dropped water droplet W can change greatly, and the contact area between the dropped water droplet W and the outer surface 31 is increased, whereby ΔT shown in the above Eq. 1 is reduced, and it becomes possible to improve the peeling resistance performance against repeated water exposure.

Therefore, it is preferable that the end face part 32 and the side face parts 33 of the protective layer 3 are configured such that the curvature radius at the minimum rounded portion 312 of the outer surface 31 is equal to or larger than 0.4 mm, and it is desirable that they have a concave shape having a contour line 311 that is smoothly continuous with the corner parts 34.

TABLE 1

| Sample No. | Curvature radius of minimum rounded portion (mm) | Number of times of water exposure |
|---|---|---|
| 1 | 0.13 | 6926 |
| 2 | 0.28 | 11281 |
| 3 | 0.38 | 56447 |
| 4 | 0.48 | 78975 |
| 5 | 0.75 | 98799 |
| 6 | 0.99 | 121456 |
| 7 | 1.64 | 134567 |
| 8 | 2.31 | 142397 |

Second Embodiment

The second embodiment according to a gas sensor element and a gas sensor will be described with reference to FIGS. 15 to 18. The gas sensor element 1 according to the first embodiment is configured such that the end face part 32 or the side face part 33 of the protective layer 3 has a concave shape which is entirely formed of a smooth curved face, and the contour line 311 of the outer surface 31 is a curved line. However, as long as it has a concave shape as a whole and is smoothly continuous with the corner parts 34, it does not necessarily have to be formed of a curved face.

The basic structures of the gas sensor element 1 and the gas sensor S of this embodiment are the same as those of the first embodiment, and their description will be omitted.

Note that, among the reference signs used in the second and following embodiments, the same reference signs as those used in the earlier embodiment(s) denote components or the like that are similar to those of the earlier embodiment(s) unless otherwise noted.

Figure 15:
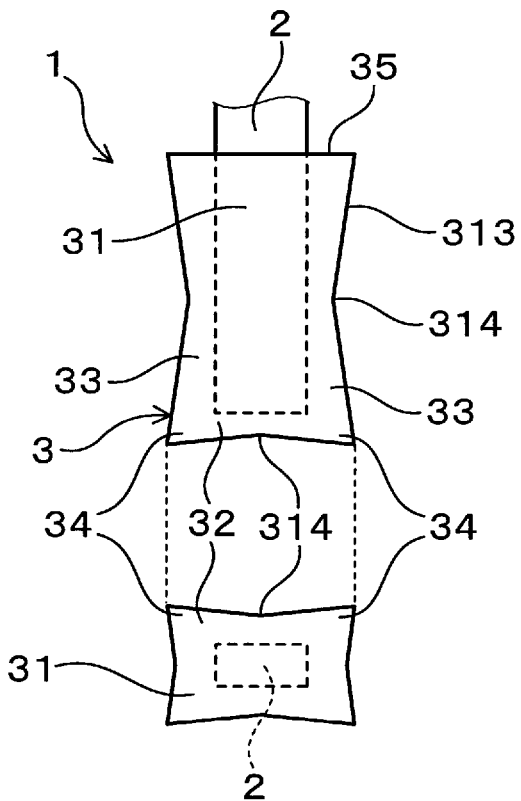
FIG. 15 is an enlarged view of the main part showing the configuration of the main part of the gas sensor element according to the second embodiment.

The gas sensor element 1 shown in FIG. 15 is configured such that the end face part 32 and the side face parts 33 of the protective layer 3 are each formed in a concave shape constituted by a combination of inclined faces. Specifically, with respect to the side face parts 33, for example, each of them may be constituted by a combination of two inclined faces in such a manner that the layer thickness is thickest at the corner part 34 on the tip end side in the longitudinal direction Z and at the end 35 on the base end side, and the layer thickness is smallest at the middle part in the longitudinal direction Z. In this case, a downward inclined face whose layer thickness gradually decreases from the corner part 34 on the tip end side and a downward inclined face whose layer thickness gradually decreases from the end 35 on the base end side are symmetrically placed, and a bend part 314 is formed at a position where the two intersect in the middle part.

Similarly, in the long side direction X or the short side direction Y perpendicular to the longitudinal direction Z, the side face part 33 may be configured such that the layer thickness gradually decreases from the corner parts 34 at the two ends toward the middle part by, for example, combining two downward inclined faces. The bend part 314 is formed at a position where the two downward inclined faces intersect in these directions as well. As a result, the downward inclined faces are combined so that the layer thickness is thickest at the four corners of the substantially rectangular side face part 33 and the layer thickness is thinnest at the center part, resulting in a concave shape as a whole that is smoothly continuous with the corner parts 34.

The end face part 32 can be configured similarly. For example, in the long side direction X and the short side direction Y, two downward inclined faces may be combined so that the layer thickness is largest at the corner parts 34 at the two ends, and the layer thickness gradually decreases toward the middle part. The bend part 314 is formed at a position where the two downward inclined faces intersect in these directions as well. As a result, the downward inclined faces are combined so that the layer thickness is thickest at the four corners of the substantially rectangular end face part 32 and the layer thickness is thinnest at the center part, resulting in a concave shape as a whole that is smoothly continuous with the corner parts 34.

Preferably, the end face part 32 or the side face part 33 has a smooth concave shape also in the case where the protective layer 3 is configured by combining a plurality of inclined faces. To achieve this, for example, the number of inclined faces constituting the end face part 32 or the side face part 33 may be increased so that there are a plurality of bend parts 314 at different locations.

Figure 16:
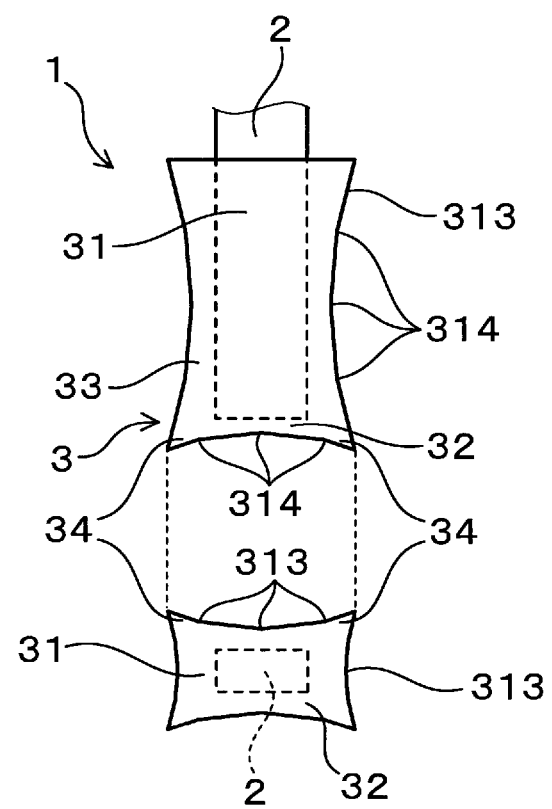
FIG. 16 is an enlarged view of the main part showing another example of the configuration of the main part of the gas sensor element according to the second embodiment.

Specifically, the gas sensor element 1 shown in FIG. 16 is configured such that each side face part 33 of the protective layer 3 has, in the longitudinal direction Z, a plurality of (for example, two in each section) downward inclined faces with different inclination angles between the corner part 34 on the tip end side or the end 35 on the base end side where the layer thickness is largest and the middle part where the layer thickness is thinnest. In this case, a plurality of (for example, three in this case) bend parts 314 are formed at positions where two adjacent inclined faces intersect.

Similarly, in the long side direction X or the short side direction Y perpendicular to the longitudinal direction Z, the side face part 33 may be configured such that the layer thickness gradually decreases from the corner parts 34 at the two ends toward the middle part by combining a plurality of (for example, 4 in total) downward inclined faces. A plurality of (for example, three in this case) bend parts 314 are formed at positions where two adjacent inclined faces intersect in these directions as well. As a result, the downward inclined faces are combined so that the layer thickness is thickest at the four corners of the substantially rectangular side face part 33 and the layer thickness is thinnest at the center part, resulting in a smoother concave shape as a whole.

The end face part 32 can be configured similarly. For example, in the long side direction X and the short side direction Y, a plurality of (for example, 4 in total) downward inclined faces may be combined so that the layer thickness is largest at the corner parts 34 at the two ends, and the layer thickness gradually decreases toward the middle part. A plurality of (for example, three in this case) bend parts 314 are formed at positions where the downward inclined faces intersect in these directions as well. As a result, the downward inclined faces are combined so that the layer thickness is thickest at the four corners of the substantially rectangular end face part 32 and the layer thickness is thinnest at the center part, resulting in a smoother concave shape as a whole.

When the end face part 32 or the side face parts 33 of the protective layer 3 has a concave shape constituted by smoothly continuous inclined faces as in the above examples, the layer thickness is largest at the corner parts 34 located on the outer peripheral edges of each face part, and it is possible to protect the element corners 23 which are the weakest parts against water exposure. In addition, since the layer thickness can be reduced at parts other than the corner parts 34, the mass of the protective layer 3 is reduced, which leads to a reduced heat capacity, and more rapid activation becomes possible. Further, when water exposure occurs, since the water droplets spread on the concave outer surface 31, an effect of suppressing the progress of peeling can be obtained.

Figure 17:
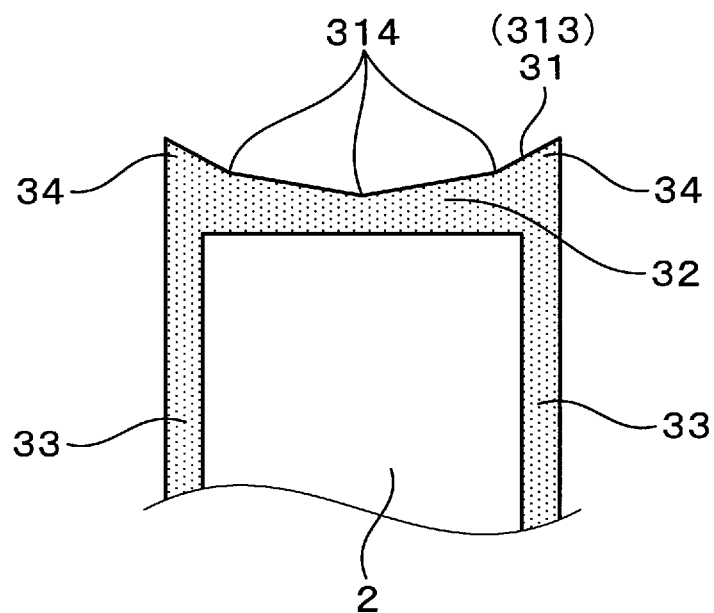
FIG. 17 is an enlarged cross-sectional view of the main part showing an example of the shape of the end face part of the protective layer of the gas sensor element according to the second embodiment.
Figure 18:
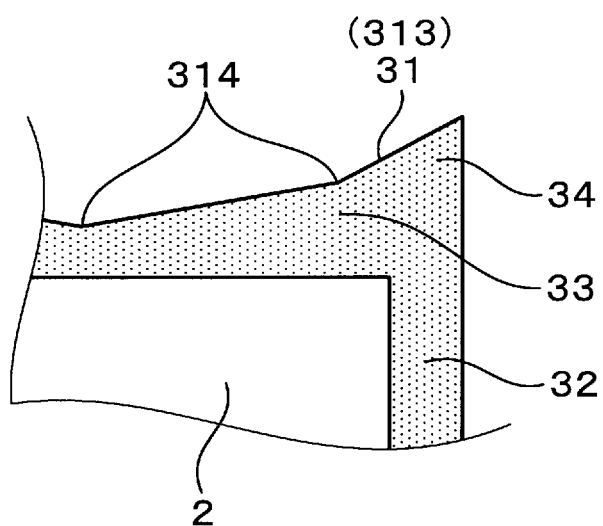
FIG. 18 is an enlarged cross-sectional view of the main part showing an example of the shape of the side face part of the protective layer of the gas sensor element according to the second embodiment.

Preferably, the outer surface 31 of each of the end face part 32 and the side face parts 33 of the protective layer 3 covering each face of the element body 2 is formed into a smooth concave shape. Here, for example, as shown in FIG. 17, a smooth concave shape indicates that, with regard to the cross section of the end face part 32 of the protective layer 3, the contour line 313 of the outer surface 31 is a combination of straight line segments that are smoothly continuous with each other between the corner parts 34 at the two ends, and it is desirable that the angles of the bend parts 314 formed by two adjacent straight line segments are large. Similarly, in the cross section of the side face part 33 of the protective layer 3 shown in FIG. 18, the contour line 313 of the outer surface 31 is a combination of straight line segments that are smoothly continuous with each other from the corner part 34 on the tip end side toward the base end side, and it is desirable that the angles of the bend parts 314 formed by two adjacent straight line segments are large.

More preferably, in the cross section of the end face part 32 of the protective layer 3 or in the cross section of the side face part 33, it is desirable that the minimum angle of the bend parts 314 formed by two adjacent straight line segments is 150° or greater. As a result, the contact area with the water droplet W increases when water exposure occurs. Thus, the water droplet easily spreads on the smooth concave outer surface 31, and the effect of suppressing the progress of peeling of the protective layer 2 is further improved.

Figure 19:
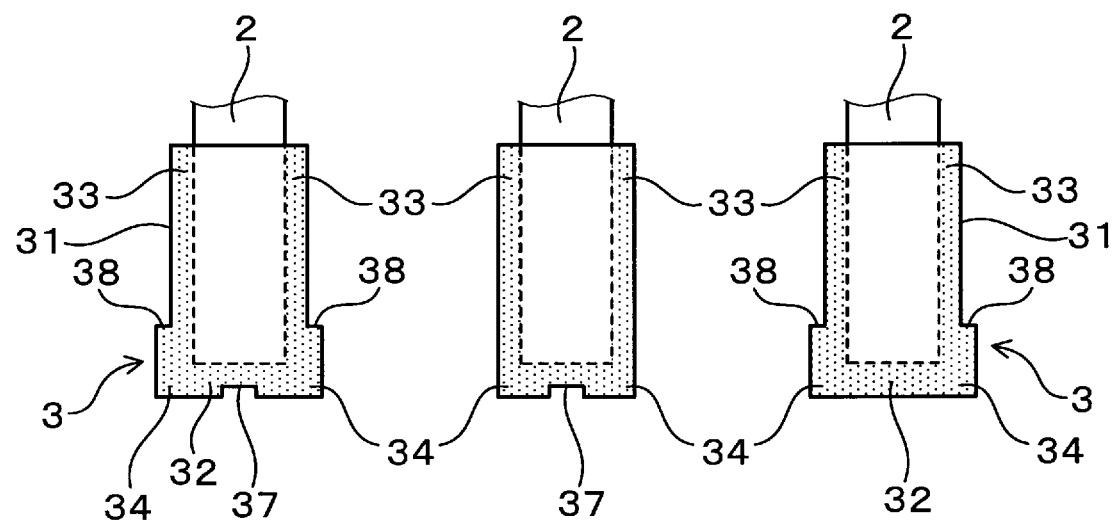
FIG. 19 is an enlarged cross-sectional view of the main part schematically showing the shape of the side face parts of the protective layer of the gas sensor element according to reference examples.
Figure 20:
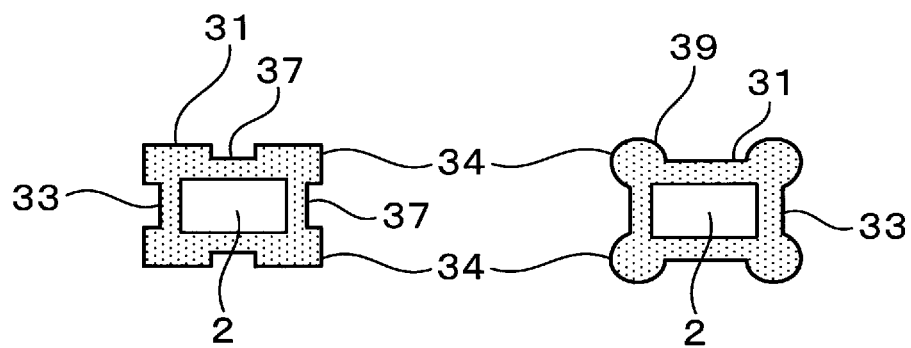
FIG. 20 is an enlarged cross-sectional view of the main part schematically showing the shape of the end face part of the protective layer of the gas sensor element according to reference examples.

As schematically shown as a reference example in FIGS. 19 and 20, as an example of a shape of the outer surface 31 of the protective layer 3 that is not smoothly continuous with the corner parts 34, the shape of the outer surface 31 of the end face part 32 or the side face parts 33 may include a step. In the middle diagram of FIG. 19, in the long side direction X, a stepped recessed part 37 is formed in the center part of the outer surface 31 of the end face part 32, and the outer surface is not smoothly continuous with the corner parts 34 at the two ends. In the right diagram of FIG. 19, in the longitudinal direction Z, the outer surface 31 of each side face part 33 on the tip end side is formed with a stepped part 38 that is bent in a stepped manner near the corner part 34, and it is not smoothly continuous with the corner part 34 on the tip end side. In the left diagram of FIG. 19, the recessed part 37 and the stepped parts 38 are formed in the end face part 32 and the side face parts 33, respectively.

Further, as shown in the left diagram of FIG. 20, in the long side direction X or the short side direction Y, a stepped recessed part 37 is formed in the center part of the outer surface 31 of the side face part 33, and the outer surface is not smoothly continuous with the corner parts 34 at the two ends. As shown in the right diagram of FIG. 20, also in a case where each of the corner parts 34 at the two ends protrudes in the form of an arc, a step 39 is formed on the outer surface 31 of the side face part 33 and it is not smoothly continuous with the corner parts 34.

When the outer surface 31 of the protective layer 3 has a shape that is not smoothly continuous with the corner parts 34 as in the above examples, the spreading of the water droplet W is suppressed and the thermal stress a tends to increase.

Experimental Example 2

Figure 21:
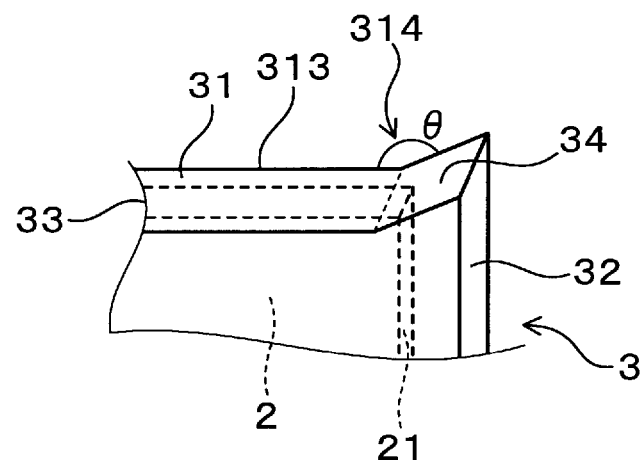
FIG. 21 is an enlarged perspective view of the main part showing the shape of the protective layers of the gas sensor element samples used in the water exposure test performed in Experimental Example 2.

Similarly to Experimental Example 1, samples of the gas sensor element 1 having the shape shown in FIG. 21 were prepared and tested to evaluate the water exposure resistance performance provided by the concave shape of the protective layer 3. In FIG. 21, the sample of the gas sensor element 1 is configured such that one of the side face parts 33 of the protective layer 3 is a concave face including an inclined face, and the contour line 313 in the cross section in the longitudinal direction Z includes a bend part 314 where straight line segments meet. The layer thickness of the protective layer 3 increases as it approaches the corner part 34 on the tip end side of the element body 2, and the layer thickness of the side face part 33 is substantially constant except for the vicinity of the corner part 34. Samples 9 to 17 were prepared by changing the shape of the inclined face that leads to the corner part 34 so that the angle θ at the bend part 314 is varied, and a repeated water exposure test was performed in the same manner as in Experimental Example 1.

In the same manner as in Experimental Example 1, a repeated water exposure test was performed, and the number of times of water exposure it took to cause peeling was evaluated.

Figure 22:
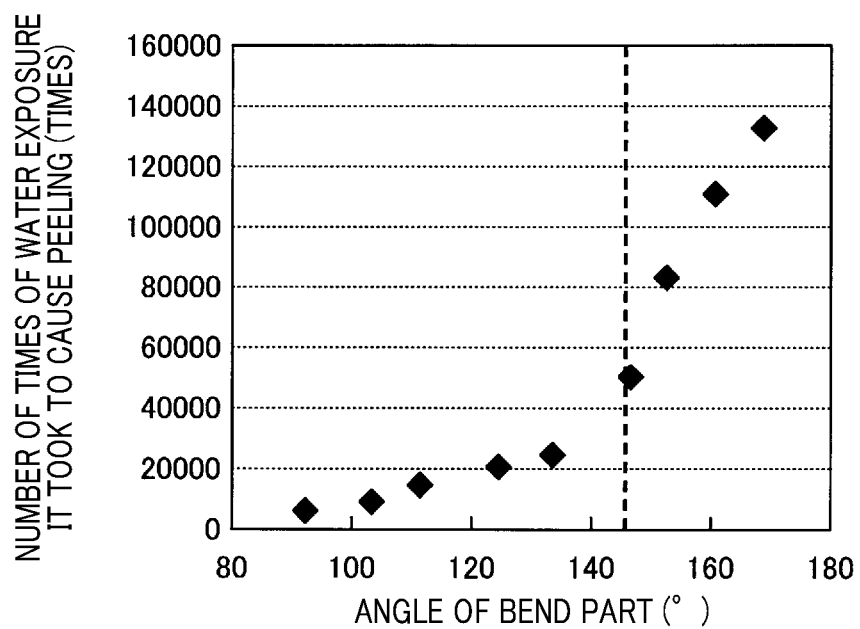
FIG. 22 is an enlarged cross-sectional view of the main part of the gas sensor element for explaining the method of the water exposure test performed in Experimental Example 2.

As shown in Table 2, the results of the repeated water exposure test show that, since the protective layer 3 formed of a concave face including an inclined face had a large layer thickness at the corner part 34, it was also capable to withstand thousands of times of repeated water exposure when 2 μL water droplet W were repeatedly dropped on the same location. Further, as shown in FIG. 22 which shows the relationship between the angle θ of the bend part 314 and the number of times of water exposure, the number of times of water exposure it took to cause peeling increases rapidly in the range where the angle θ is 150° or greater. This indicates that the shape of a dropped water droplet W can change greatly on a concave surface having a large angle θ of the bend part 314 so that it is smoothly continuous with the corner part 34. Then, the contact area between the water droplet W and the outer surface 31 is increased, whereby ΔT shown in the above Eq. 1 is reduced, and it becomes possible to improve the peeling resistance performance against repeated water exposure.

Thus, preferably, the end face part 32 and the side face parts 33 of the protective layer 3 are configured such that the minimum angle of the bend part(s) 314 formed on the outer surface 31 is 150° or greater in order to form a concave shape having a contour line 313 that is smoothly continuous with the corner parts 34.

TABLE 2

| Sample No. | Angle of bend parts (°) | Number of times of water exposure |
|---|---|---|
| 9 | 92 | 6874 |
| 10 | 103 | 9784 |
| 11 | 111 | 15478 |

TABLE 2-continued

| Sample No. | Angle of bend parts (°) | Number of times of water exposure |
|---|---|---|
| 12 | 124 | 21457 |
| 13 | 133 | 25415 |
| 14 | 146 | 51356 |
| 15 | 152 | 84567 |
| 16 | 160 | 112456 |
| 17 | 168 | 134578 |

In the above-described first and second embodiments, the end face part 32 and the side face parts 33 of the protective layer 3 have a concave shape with a smooth curved face, or a concave shape with a plurality of inclined faces that are smoothly continuous with each other. However, it is also possible to combine these to form a concave shape.

Note that the present disclosure is not limited only to the embodiments, and other embodiments can be implemented without deviating from the gist thereof. Further, the structures of the gas sensor element 1 and the gas sensor S are not limited to those shown in the above embodiments, and for example, the configuration of the element cover and other parts can be appropriately changed according to the application. Furthermore, the gas to be measured is not limited to exhaust gas from an automobile engine, and the specific gas component may also be any gas component.

What is claimed is:

1. A gas sensor element comprising a long plate-like element body and a porous protective layer protecting a surface of the element body, wherein
the element body has a gas detection part at an end thereof on one end face side in a longitudinal direction, and
the protective layer includes an end face part covering the one end face in laminate, side face parts covering side faces connected to the one end face in laminate, and corner parts where two adjacent ones of the end face part and the side face parts meet, and an outer surface of at least the end face part of the protective layer has a concave shape that is smoothly continuous with the corner parts and a layer thickness of at least the end face part of the protective layer increases toward the corner parts from a center of the one end face part of the protective layer in the longitudinal direction.

2. The gas sensor element according to claim 1, wherein the outer surface of the protective layer has a concave shape that is smoothly continuous with the corner parts at each of the end face part and the side face parts.

3. The gas sensor element according to claim 1, wherein the outer surface has a concave shape having a smooth curved surface.

4. The gas sensor element according to claim 1, wherein, in a cross section in the longitudinal direction or in a direction orthogonal to the longitudinal direction, the outer surface has a contour line including a smoothly continuous curved line.

5. The gas sensor element according to claim 4, wherein the outer surface is configured such that a curvature radius at a minimum rounded portion of the contour line is equal to or larger than 0.4 mm.

6. The gas sensor element according to claim 1, wherein the outer surface has a concave shape having a plurality of inclined faces that are smoothly continuous with each other.

7. The gas sensor element according to claim 1, wherein, in a cross section in the longitudinal direction or in a direction orthogonal to the longitudinal direction, the outer surface has a contour line including a combination of a plurality of straight line segments that are continuous with each other.

8. The gas sensor element according to claim 7, wherein the outer surface is configured such that a bend part formed in the contour line has a minimum angle of 150° or larger.

9. A gas sensor comprising the gas sensor element according to claim 1 to detect a specific gas component in a gas to be measured, the gas sensor further comprising
- a cylindrical housing supporting an outer periphery of the gas sensor element, and a cover body attached to one end of the cylindrical housing, wherein an end of the gas sensor element at which the protective layer is provided is housed in the cover body, and the measured gas is introduced into the cover body through a through hole provided in the cover body.

10. The gas sensor element according to claim 1, wherein
- the outer surface of each of the end face part and the side face parts of the protective layer covering each face of the element body is formed into a concave shape that is smoothly continuous with the corner parts.

11. The gas sensor element according to claim 10, wherein
- an entire face of the outer surface of each of the end face part and the side face parts of the protective layer is a smooth curved surface connected to the corner parts.

12. The gas sensor element according to claim 1, wherein the outer surface of at least the end face part of the protective layer being concave inward toward the one end face side of the gas detection part in the longitudinal direction.

* * * * *